(12) United States Patent
Friedman et al.

(10) Patent No.: US 8,961,543 B2
(45) Date of Patent: Feb. 24, 2015

(54) TISSUE LIGATION DEVICES AND METHODS

(75) Inventors: Paul A. Friedman, Rochester, MN (US); Charles J. Bruce, Rochester, MN (US); Samuel J. Asirvatham, Rochester, MN (US); Trevor A. McCaw, Vancouver (CA); Elliot Y. K. Hong, Vancouver (CA)

(73) Assignees: Mayo Foundation for Medical Education and Research, Rochester, MN (US); Aegis Medical Innovations Inc., Vancouver, B.C. (CA)

( * ) Notice: Subject to any disclaimer, the term of this patent is extended or adjusted under 35 U.S.C. 154(b) by 980 days.

(21) Appl. No.: 13/124,950

(22) PCT Filed: Oct. 20, 2009

(86) PCT No.: PCT/US2009/061267
§ 371 (c)(1),
(2), (4) Date: Aug. 10, 2011

(87) PCT Pub. No.: WO2010/048141
PCT Pub. Date: Apr. 29, 2010

(65) Prior Publication Data
US 2012/0022558 A1    Jan. 26, 2012

Related U.S. Application Data (60) Provisional application No. 61/106,761, filed on Oct. 20, 2008.

(51) Int. Cl.
| | |
|---|---|
| A61B 17/04 | (2006.01) |
| A61B 17/12 | (2006.01) |
| A61B 17/00 | (2006.01) |

(52) U.S. Cl.
CPC ....... *A61B 17/12013* (2013.01); *A61B 17/0487* (2013.01); *A61B 2017/00867* (2013.01); *A61B 2017/0475* (2013.01); *A61B 2017/0488* (2013.01); *A61B 2017/0496* (2013.01)
USPC ........................................... 606/144

(58) Field of Classification Search
USPC ................... 606/139–141, 144, 148
See application file for complete search history.

(56) References Cited

U.S. PATENT DOCUMENTS

| | | |
|---|---|---|
| 2,610,631 A | 9/1952 | Calicchio |
| 3,476,115 A | 11/1969 | Graeff et al. |

(Continued)

FOREIGN PATENT DOCUMENTS

| | | |
|---|---|---|
| JP | 2003-204966 A | 7/2003 |
| WO | WO 2008/036408 A2 | 3/2008 |
| WO | WO 2008/036408 A3 | 8/2008 |

OTHER PUBLICATIONS

U.S. Appl. No. 61/175,199, filed May 4, 2009, McCaw et al.

(Continued)

*Primary Examiner* — Dianne Dornbusch
(74) *Attorney, Agent, or Firm* — Mueting, Raasch & Gebhardt, P.A.

(57) ABSTRACT

Devices and methods for ligating structures where the loop of the ligation element can be temporarily pre-tightened without locking the loop. This pre-tightening without locking allows the loop of the ligation element to be loosened and repositioned, if necessary, before locking the loop around the anatomical structure.

9 Claims, 7 Drawing Sheets

(56) References Cited

U.S. PATENT DOCUMENTS

| | | | |
|---|---|---|---|
| 5,144,961 A | | 9/1992 | Chen et al. |
| 5,171,314 A | * | 12/1992 | Dulebohn ............... 606/113 |
| 5,242,459 A | | 9/1993 | Buelna |
| 5,300,078 A | * | 4/1994 | Buelna ............... 606/113 |
| 5,312,423 A | | 5/1994 | Rosenbluth et al. |
| 5,330,491 A | * | 7/1994 | Walker et al. ............... 606/148 |
| 5,562,684 A | * | 10/1996 | Kammerer ............... 606/139 |
| 5,716,367 A | * | 2/1998 | Koike et al. ............... 606/144 |
| 5,759,189 A | | 6/1998 | Ferragamo et al. |
| 5,792,151 A | * | 8/1998 | Heck et al. ............... 606/144 |
| 5,908,429 A | * | 6/1999 | Yoon ............... 606/144 |
| 5,928,250 A | * | 7/1999 | Koike et al. ............... 606/139 |
| 6,132,439 A | | 10/2000 | Kontos |
| 6,379,366 B1 | * | 4/2002 | Fleischman et al. ............... 606/139 |
| 7,063,661 B2 | * | 6/2006 | Okada ............... 600/127 |
| 7,101,378 B2 | * | 9/2006 | Salameh et al. ............... 606/113 |
| 2002/0099390 A1 | * | 7/2002 | Kaplan et al. ............... 606/139 |
| 2003/0144673 A1 | * | 7/2003 | Onuki et al. ............... 606/139 |
| 2005/0143767 A1 | | 6/2005 | Kimura et al. |
| 2005/0251153 A1 | * | 11/2005 | Sakamoto et al. ............... 606/139 |
| 2008/0243183 A1 | * | 10/2008 | Miller et al. ............... 606/228 |
| 2009/0105730 A1 | | 4/2009 | Onuki et al. |

OTHER PUBLICATIONS

Written Opinion of the International Searching Authority issued Jun. 9, 2010, by the PCT, Patent Application No. PCT/US2009/061267, filed Oct. 20, 2009.

* cited by examiner

TISSUE LIGATION DEVICES AND METHODS

RELATED APPLICATION

This application is a U.S. National Stage Application of International Application No. PCT/US2009/061267, titled TISSUE LIGATION DEVICES AND METHODS, filed on Oct. 20, 2009, published in the English language on Apr. 29, 2010 as International Publication No. WO 2010/048141 A2, which claims the benefit under 35 U.S.C. §119(e) of U.S. Provisional Patent Application No. 61/106,761 titled TISSUE LIGATION DEVICES AND METHODS and filed Oct. 20, 2008, which is hereby incorporated by reference in its entirety.

Tissue ligation devices and methods are described herein. More specifically, the devices described herein can be used to pre-tighten ligation elements, e.g., sutures, prior to final fastening and/or locking.

Ligation devices including various features have previously been described. For example, a suture applying device having a slidably mounted cutting member as been described in U.S. Pat. No. 5,242,459 to Buelna, issued on Sep. 7, 1993, and entitled "Device and Method for Applying a Ligating Loop." Further, for example, a tubular device for applying a loop of suture having a free end of the suture attached to a frangible proximal end of the tube has been described in U.S. Pat. No. 3,476,115 to Graeff et al., issued on Nov. 4, 1969, and entitled "Ligating Implement with Ligature Severing Means." Still further, for example, a ligating device where a loop having a pre-tied knot that may be tightened by retracting a slidable member that draws back a free end of the loop as been described in U.S. Pat. No. 2,410,631 to Calicchio, issued to Sep. 16, 1952, and entitled "Ligator."

SUMMARY

The devices and methods described herein provide for the ligating of structures (e.g., anatomical structures) where the loop of the ligation element can be temporarily pre-tightened without locking the loop. This pre-tightening without locking allows the loop of the ligation element to be loosened and repositioned, if necessary, before locking the loop around the anatomical structure.

In one aspect, a ligation device as described herein may include a pre-tightening sheath, a ligation element, a locking element, a pushing member, and an optional restraining mechanism. The pre-tightening sheath may include a proximal end, a distal end, a longitudinal axis extending between the proximal end and the distal end, an opening proximate the distal end of the sheath, and a lumen extending through the sheath from the opening towards the proximal end of the sheath. The ligation element may include a loop. Further, at least a portion of the ligation element may be located within the lumen of the pre-tightening sheath when the loop extends out of the opening in the pre-tightening sheath. Still further, the opening in the pre-tightening sheath and the ligation element may be sized to allow movement between the pre-tightening sheath and the ligation element to tighten and loosen the loop around a structure located within the loop. The locking element may be located within the lumen of the pre-tightening sheath, and further may be operable to retain the loop of the ligation element in a selected size after removal of the ligation element from the pre-tightening sheath. The pushing member may include a proximal end and a distal end. At least a portion of the pushing member may be located within the lumen of the pre-tightening sheath. Further, the pushing member may advance the locking element towards the loop of the ligation element when the distal end of the pushing member advances towards the opening of the pre-tightening sheath. Relative movement of the pre-tightening sheath and the ligation element along the longitudinal axis changes the size of the loop.

The restraining mechanism, if provided, may be operable between a closed configuration and an open configuration. When in the closed configuration, the restraining mechanism may restrict relative movement between the pre-tightening sheath and the ligation element along the longitudinal axis. When in the open configuration, the restraining mechanism may allow relative movement between the pre-tightening sheath and the ligation element along the longitudinal axis. Further, the restraining mechanism may be located proximate the proximal end of the pre-tightening sheath.

Still further, the pushing member may include an opening proximate the distal end of the pushing member, and a lumen extending through the pushing member from the opening towards the proximal end of the sheath. Yet still further, at least a portion of the ligation element may be located within the lumen of the pushing member.

In another aspect, a ligation device as described herein may include a pushing member, a two-way locking element, and a ligation element. The pushing member may include a proximal end, a distal end, and a longitudinal axis extending between the proximal end and the distal end. The two-way locking element may be located proximal the distal end of the pushing member and may include at least one passage. The ligation element may include a loop and at least a portion of the ligation element may located within the at least one passage of the two-way locking element. Further, the two-way locking element may be operable between a closed configuration and an open configuration. When in the closed configuration, the two-way locking element may allow movement of the ligation element to tighten the loop around a structure located within the loop. When in the open configuration, the two-way locking element may allow movement of the ligation element to tighten or loosen the loop around the structure located with the loop.

In another aspect, a ligation device as described herein may include a pre-tightening sheath, a ligation element, a locking element, and a pushing member. The pre-tightening sheath may include a proximal end, a distal end, a longitudinal axis extending between the proximal end and the distal end, an opening proximate the distal end of the sheath, and a lumen extending through the sheath from the opening towards the proximal end of the sheath. The ligation element may include a loop. Further, at least a portion of the ligation element may be located within the lumen of the pre-tightening sheath when the loop extends out of the opening in the pre-tightening sheath. Still further, the opening in the pre-tightening sheath and the ligation element may be sized to allow movement along the longitudinal axis between the pre-tightening sheath and the ligation element to tighten and loosen the loop around a structure located within the loop. The locking element may be located within the lumen of the pre-tightening sheath and may be operable to retain the loop of the ligation element in a selected size after removal of the ligation element from the pre-tightening sheath. The pushing member may include a proximal end and a distal end. Further, at least a portion of the pushing member may be located within the lumen of the pre-tightening sheath and the pushing member may have an interference fit within the pre-tightening sheath. Still further, the pushing member may advance the locking element towards the loop of the ligation element when the distal end of the pushing member advances towards the opening of the pre-tightening sheath. Relative movement of the pre-tightening sheath and the ligation element along the longitudinal axis changes the size of the loop.

In another aspect, a method as described herein may include using a ligation device to tighten a ligation loop around a structure. The method may include providing a ligation device and positioning the loop of the ligation element around the structure. Further, the method may include tightening the loop of the ligation element by moving the pre-tightening sheath and the ligation element relative to each other along a longitudinal axis extending through the pre-tightening sheath. Still further, the method may include locking the loop of the ligation element around the structure with the locking element.

If an operator is not satisfied with the positioning of the loop, for example, the method may further include loosening the loop of the ligation element after the tightening and repositioning the loop of the ligation element around a structure. Further, the loosening may include moving the pre-tightening sheath and the ligation element relative to each other along the longitudinal axis.

The above summary is not intended to describe each embodiment or every implementation of the present invention. Rather, a more complete understanding of the invention will become apparent and appreciated by reference to the following Description of Exemplary Embodiments and claims in view of the accompanying figures of the drawing.

DETAILED DESCRIPTION OF EXEMPLARY EMBODIMENTS

In the following detailed description of exemplary embodiments, reference is made to the accompanying figures of the drawing which form part hereof, and in which are shown, by way of illustration, specific embodiments which may be practiced. It is to be understood that other embodiments may be utilized and structural changes may be made without departing from the scope of the present invention. Unless stated otherwise herein, the figures of the drawing are rendered primarily for clarity and thus may not be drawn to scale.

As used herein, "a," "an," "the," "at least one," and "one or more" are used interchangeably. The term "and/or" (if used) means one or all of the listed elements or a combination of any two or more of the listed elements.

As described herein, the devices and methods described herein can be used to tighten a ligation loop around any structure, although in some embodiments, the devices and methods described herein may be used to tighten a ligation loop around an anatomical structure. As used herein, the term "anatomical structure" may be defined as any anatomical and/or pathological structure, e.g., the left atrial appendage (LAA), the gallbladder, the GI appendage, diverticula, fallopian tubes, ovaries, vascular aneurysm, any pedunculated structure or mass, etc.

Figure 1:
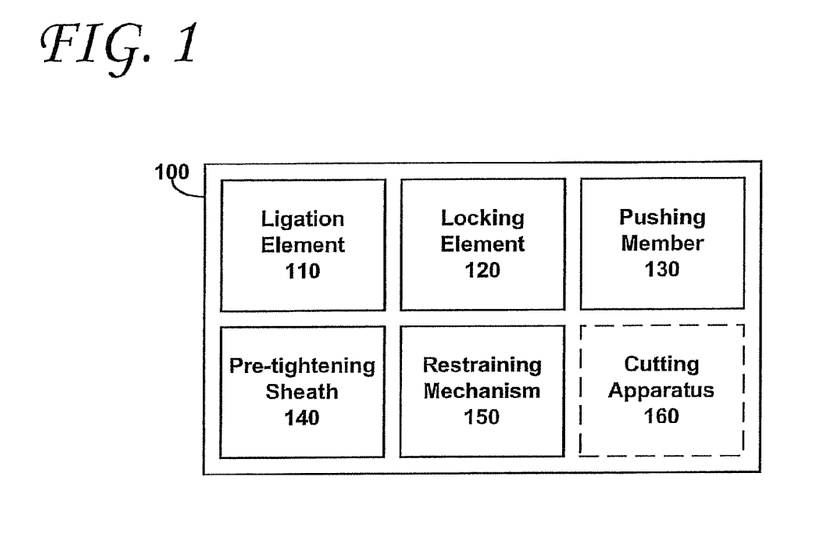
FIG. 1 is a diagrammatic representation of an exemplary embodiment of the ligation device as described herein.

FIG. 1 is a diagrammatic representation of a ligation device 100. The ligation device may include a ligation element 110, a locking element 120, a pushing member 130, a pre-tightening sheath 140, and a restraining mechanism 150.

The ligation device 100 may be used, e.g., to fasten, approximate, and/or ligate anatomical structures and may be configured for catheter, endoscopic, and/or open surgical procedures on any site within a patient or animal. Further, the ligation device may be designed to be flexible (e.g., non-rigid) to accommodate any working channel without a direct line of sight access.

The ligation device 110 may, e.g., have a length between about 5 centimeters (cm) and about 100 cm and may have a diameter between about 0.05 cm and about 1.0 cm.

The ligation device 100 may be used with any tissue approximation or ligation techniques including, but not limited to, the following techniques: suture loop with or without a pre-tied knot; suture loop with a mechanical suture fastening device; a wire loop with a mechanical fastening device; wire loop with a ratchet locking mechanism; and/or a partial loop with enough mechanical support to support pre-tightening. Further, any combination of materials used in surgical procedures for tissue approximation or ligating tissue may be utilized with the present devices.

The ligation element 110 may include a suture loop, wire snare, hollow suture (e.g., a soft pliable suture having a hollow core within which a more rigid, removable control element extends—as described in, e.g., International Publication WO 2008/036408 titled DEVICES AND METHODS FOR LIGATING ANATOMICAL STRUCTURES), band, elastic, etc. The ligation element 110 may be formed of, e.g., a monofilament and/or braided suture and may include materials such as, e.g., polyester, PTFE, polyethylene, nylon, polypropylene, metal, and/or any other suitable material used in surgical applications as known by one having ordinary skill in the art. Further, the material of the ligation element 110 may be absorbable (e.g., material that may break-down within a body without intervention) or non-absorbable. In at least one embodiment, the ligation element 110 may include shape memory materials such as, e.g., Nitinol.

The locking element 120 may include a sliding knot, a suture locking device, a suture anchor, one-way sliding knot, a ratcheting mechanism, adhesive, a weld created using radio frequency (RF) energy, a weld created using ultrasound energy, cryo-activated weld/bond, etc. Further, the locking element 120 may be a one-way lock (e.g., a lock that can only move in one direction along the ligation element) or a two-way lock (e.g., a lock that can move in both directions along the ligation element). Still, further, the locking element 120 may include an active locking mechanism (e.g., a movable pin to secure the suture) or passive locking mechanism (e.g., an opening that only allows the suture to move in a single direction). Some potentially suitable suture locks that may be used in connection with devices and methods described herein are described in U.S. Provisional Patent Application No. 61/175,199 entitled SUTURE LOCK AND SUTURE LOCK SYSTEMS filed on May 4, 2009.

In one or more embodiments, the locking element 120 may be integrated with the ligation device 100 such that it may be deployed by an operator with single-handed operation. Further, in one or more embodiments, the ligation device 100 may not include a locking element. For example, an operator may only intend to temporarily ligate tissue and/or an operator may attach a locking device to the ligation element using another instrument and/or method (e.g., using an extracorporeally tied knot).

The pushing member 130 may be capable of advancing the locking element 120 to secure the ligation element 110 around, e.g., an anatomical structure. Further, the pushing member 130 may be a catheter-like structure extending from a proximal end to a distal end. The pushing member 130 may include a lumen within which the ligation element 110 may be located.

The pre-tightening sheath 140 may also be a catheter-like structure extending from a proximal end to a distal end and may include a lumen within which the pushing element 130 may be located. The pre-tightening sheath 140 may be designed to allow a user to test the positioning of the ligation element 110 prior to the locking or fastening of the ligation element 110 with, e.g., the locking element 120. For example, the pre-tightening sheath 140 may advance in the longitudinal direction along a longitudinal axis over the distal end of the pushing member 130 and the locking element 120 contact, e.g., a loop of the ligation element 110 to tighten the loop of the ligation element 110 around, e.g., an anatomical structure.

In one or more embodiments, advancement of the pre-tightening sheath 140 along the longitudinal axis may be used to temporarily ligate the tissue, providing an operator with an opportunity to decide whether to deploy a fastening/locking device after reviewing the results of the temporary tissue ligation. For example, an operator may advance the pre-tightening sheath along the longitudinal axis to temporarily ligate an anatomical structure and review the results using various visualizations and diagnostics, such as, e.g., fluoroscopy, ultrasound, magnetic resonance imaging (MRI), computerized tomography (CT), endoscopy, direct visualization, patient feedback, x-ray, biomarkers, etc. Then, if the operator is satisfied with the results, the operator may secure the ligation element in place by any suitable technique, e.g., tie a knot, deploy a suture lock, etc.

Further, in one or more embodiments, the ligation device 100 may be designed to limit the degree to which an operator can pre-tighten the ligation element 110 with the pre-tightening sheath 140. For example, the pre-tightening sheath 140 may be designed such that there is a maximum force that it may apply to the ligation element 110. The ligation device 100 may include, e.g., springs, elastic/deformable materials, limiting structures, etc. to, for example, limit the maximum force that may be applied to the ligation element 110. In at least one embodiment, the outer surface of the pushing member 130 and/or the inside lumen surface of the pre-tightening sheath 140 may be tapered, or include various tapers, rings, stop surfaces, etc. that may hinder the advancement of the pre-tightening sheath 140 along the longitudinal axis to, e.g., limit the maximum force that may be applied to the ligation element 110.

Still further, in one or more embodiments, the ligation device may have maximum thresholds, minimum thresholds, or both for the size of the loop of the ligation element because, e.g., certain anatomical structures may be damaged if the loop of a ligation element becomes too restrictive and/or too small (e.g., a suture loop may be intended to maintain blood flow and/or prevent necrosis if temporarily ligating various anatomical structures).

The ligation device 100 may optionally include a restraining mechanism 150 that may be operable to secure the movement of the pre-tightening sheath 140 relative to the pushing member 130. The restraining mechanism 150 may be trigger lock, thumb lock, screw lock, pivoting tab, collet and nut, etc. In at least one embodiment, the restraining mechanism may be an interference fit between the pushing member 130 and the pre-tightening sheath 140. For example, the pushing member 130 may fit within the lumen of the pre-tightening sheath 140 with an interference fit that provides sufficient friction between the pushing member/ligation element and the pre-tightening sheath such that relative movement between the two components along a longitudinal axis extending through the sheath is restrained.

As used herein, the phrase "interference fit" refers to the coupling of a male member (e.g., the pushing member) having a dimension larger than an undeflected or undeformed dimension of a mating female receptacle (e.g., the pre-tightening sheath) such that one or both of the male and female members deforms during assembly. As a result, a substantially tight fit may be obtained such that the male member does not move relative to the female member and/or the female member does not move relative to the male member without external forces applied to either the male or female member.

In at least another embodiment of a restraining mechanism, an exterior surface of the pushing member and the interior surface of the lumen of the pre-tightening sheath may be threaded resulting in a screw-feed mechanism for advancing and/or retracted the pushing member and or pre-tightening sheath relative to each other.

The ligation device 100 may optionally include cutting apparatus 160. The cutting apparatus 160 may allow an operator to cut the tails of the ligation element. The cutting apparatus 160 may be actuated by the same movements as the pre-tightening, or different movements, or the cutting may be performed by a separate instrument altogether. In other embodiments, the locking device may function to cut the tails of the ligation element while being deployed, when the device has finished locking, while the locking device is being actuated, etc.

Although described together in this embodiment, the different elements of ligation device 100, e.g., the pre-tightening sheath, may be configured to work with many other medical instruments that may benefit from their operation. Further, the ligation device 100 may be used in conjunction with any other medical instrument as would be recognized by one having ordinary skill in the art, e.g., endoscopes, suction catheters, forceps, cryogenic-tipped catheters, etc.

Figure 2A:
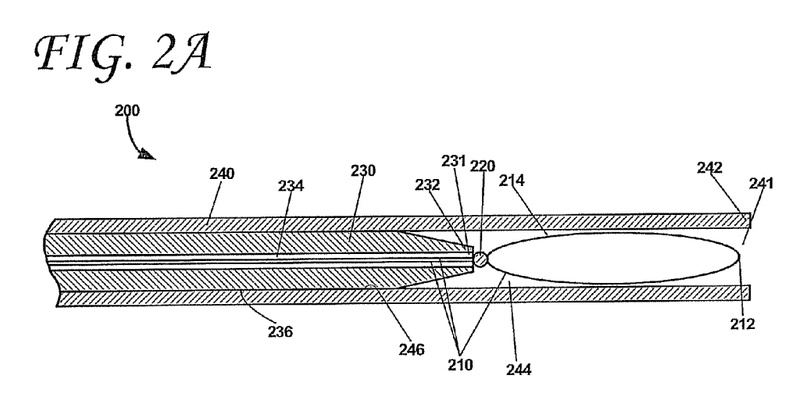
FIG. 2A illustrates a cross-sectional view of an exemplary embodiment of a ligation device in a pre-deployment position.

FIG. 2A illustrates a cross-sectional view of an exemplary embodiment of a ligation device 200 in a pre-deployment position. The ligation device 200 includes a ligation element 210, a locking element 220, pushing member 230, and a pre-tightening sheath 240. A longitudinal axis extends between the proximal and distal ends of the ligation device 200.

The ligation element 210 may extend from a proximal end (not shown) to a distal end 212. The proximal end of any portion of the ligation device 200 refers to the end that would be farthest away from the anatomical structure when the ligation device 200 is being utilized, and the distal end refers to the end that would be proximate to the anatomical structure when the ligation device 200 is being utilized.

Further, the ligation element 210 passes through the lumen 234 of the pushing member 230, extends out the opening 231 at the distal end 232 of the pushing member 230, and further extends through the locking element 220. The tails of the ligation element 210 may be long enough to exit out of the proximal end of the ligation device 200 such that, e.g., an operator may manipulate them directly. The distal end 212 of the ligation element 210 preferably fauns a loop 214. In this embodiment, the loop 214 is the portion of the ligation element 210 that extends past the locking element 220. However, the loop 214 may change size and/or location depending on the various stages of deployment the ligation device 200 is undergoing.

Although the ligation element 210 depicted in FIGS. 2A-G is a single strand doubled-back on itself, in other embodiments the ligation element may be provided in other configurations, e.g., a single strand extending in the proximal direction with a loop attached proximate the distal end of the single strand, etc.

Locking element 220 may be located proximate the distal end 232 of the pushing member 230. In one or more embodiments, the locking element 220 may be releasably attached to the distal end 232 of the pushing member 230.

As used herein, the term "releasably attached" may be defined as being attached in way such that the locking element 220 may be selectively detached, e.g., by an operator, after a period of time, under a certain amount of force, etc., while the locking element 220 is in use during deployment of the ligation element 210 about the selected anatomical tissue.

Although depicted in this embodiment as a round member, the locking element 220 may take any form such as, e.g., a sliding knot, a suture locking device, a suture anchor, adhesive, RF weld, ultrasonic weld, cryo weld/bond, etc.

If adhesive is to be used as, or in connection with, the locking element 220, the pushing member 230, pre-tightening sheath 240, and/or any other apparatus described herein may include one or more reservoirs or bladders containing adhesive to be utilized in connection with the locking element. Alternatively, the pushing member 230 and/or pre-tightening sheath 240 may include one or more lumens used to deliver the adhesive to the selected location. Further, at least in another embodiment, the pushing member 230, pre-tightening sheath 240, and/or any other apparatus provided in connection with the ligation device may include other elements, e.g., electrodes for delivering energy (e.g., radio-frequency energy) to weld/fuse the ligation element, and/or a locking element to lock the loop of the ligation element in a selected size.

The pushing member 230 may extend from a proximal end (not shown) to a distal end 232 and may define a lumen 234 and an opening 231. In this embodiment, the distal end 232 of the pushing member includes an optional taper. In other embodiments, the distal end 232 may take any shape (preferably atraumatic) operable to push the locking element 220 along the ligation element 210 to tighten the loop of the ligation element 210. The pushing member 230 may further define an exterior surface 236 that may engage the interior lumen surface 246 of the pre-tightening sheath 240. As described herein, the contact between the pushing member 230 and the pre-tightening sheath 240 may result in an interference fit. In other embodiments, a gap may exist between the pushing member 230 and the pre-tightening sheath 240. In some embodiments, any such gap may be large enough and/or shaped to allow additional instruments and/or the ligation element 210 to extend through the pre-tightening sheath 240 outside of the pushing member 230.

The pushing member 20 may be formed of a substantially rigid material, a flexible material (e.g., polypropylene or polyethylene), or a combination of flexible and rigid materials.

In at least one embodiment, either the interior lumen surface 246 of the pre-tightening sheath 240 and/or the exterior surface 236 of the pushing member 230 may be tapered such that when the pre-tightening sheath 240 is moved along the longitudinal axis relative to the pushing member 230 towards the anatomical structure 250, the resistance of movement between the pre-tightening sheath 240 and the pushing member 230 may increase. Such increase in resistance may provide an operator tactile feedback on, e.g., ligation tension, loop size, etc.

The pre-tightening sheath 240 may extend from a proximal end (not shown) to a distal end 242 and may define a lumen 244 that has an interior lumen surface 246, an opening 241 and a longitudinal axis extending between the proximal end and the distal end 242. The distal end 242 may preferably take any atraumatic shape operable for extending the ligation device 200 to an anatomical structure to be ligated. In FIG. 2A, when the ligation device 200 is in a pre-deployment position, at least a portion of the ligation element 210, the locking element 220, and at least a portion of the pushing member 230 may be located within the lumen 244 of the pre-tightening sheath 240. Further, the loop 214 of the ligation element 210 may be in a deflected state as shown in FIG. 2A, e.g., the loop 214 may be compressed by the interior lumen surface 246 of the pre-tightening sheath 240.

Figure 2B:
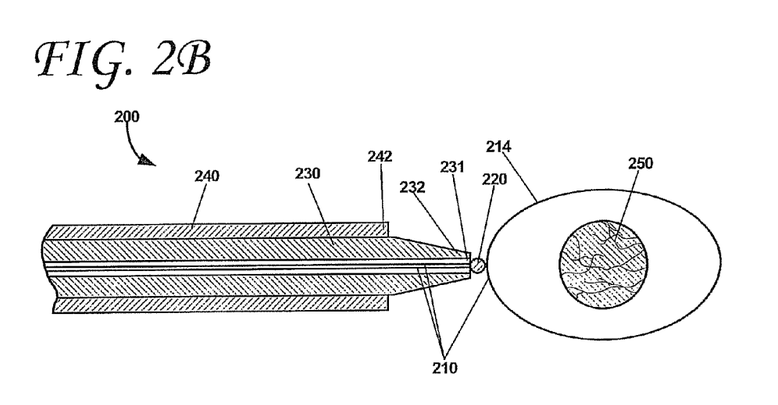
FIG. 2B illustrates a cross-sectional view of the exemplary embodiment of the ligation device of FIG. 2A as the loop of the ligation element is positioned around a structure.

The ligation device 200 is shown in a deployed position in FIG. 2B, i.e., a position in which the pre-tightening sheath 240 is positioned to expose the distal end 232 of the pushing member 230. This position may be used, e.g., when positioning the loop 214 of the ligation element 210 around an anatomical structure 250.

In at least one embodiment, the loop 214 of the ligation element 210 can be adapted for placement around, e.g., the LAA (e.g., the base of the LAA), such that the LAA can be effectively closed off from the left atrium. Further, the ligation element 210 may be constructed to be rigid and/or to have shape memory, such that the ligation element may have a closed, deflected configuration for passage through the pushing member (e.g., FIG. 2A) and/or pre-tightening sheath 240, and an open loop configuration for placement over and around an anatomical structure (e.g., FIG. 2B).

The loop 214 of the ligation element 210 may take any suitable shape and size. For example, the loop 214 may have an essentially circular or oval shape, or can have an irregular shape to, for example, follow the curve of the heart. Further, the loop 214 may have, e.g., a maximum diameter from about 0.5 cm to about 4 cm (e.g., from about 0.7 cm to about 3.5 cm, from about 1.0 cm to about 2.5 cm, or from about 1.5 cm to about 2.0 cm).

In at least one embodiment, the shape memory material of the ligation element can be configured such that as the ligation element is progressively advanced from the distal end of the ligation device, the shape and angulation of the loop changes. Further, the angulation and/or shape of the ligation element can, in some embodiments, be tailored based on patient anatomy. Angled configurations of the ligation element can potentially provide additional control over the loop to further facilitate positioning of the device.

The loop 214 of the ligation element 210 may be resilient, and as shown in FIG. 2B, upon leaving the lumen 244 of the pre-tightening sheath 240, the loop 214 may rebound from the deflected position shown in FIG. 2A to an undeflected position shown in FIG. 2B.

Figure 2C:
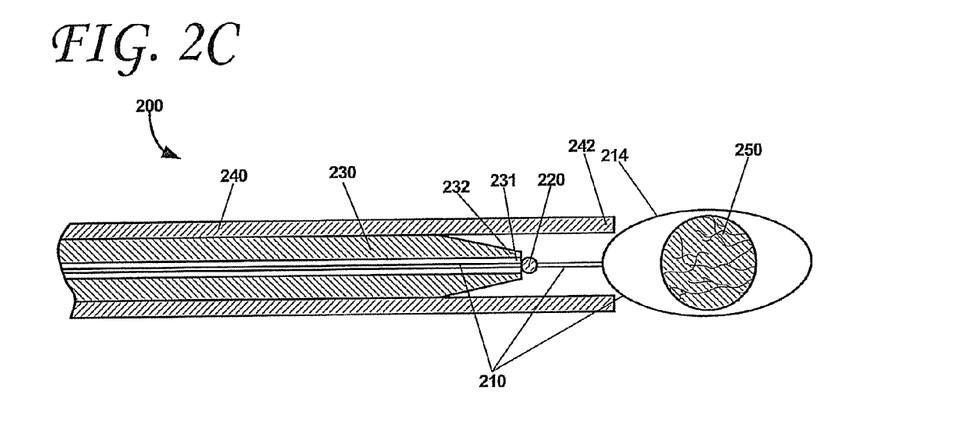
FIG. 2C illustrates a cross-sectional view of the exemplary embodiment of the ligation device of FIG. 2A as the pre-tightening sheath is advanced to pre-tighten the ligation element around the structure.

In FIG. 2C, the pre-tightening sheath 240 has engaged the ligation element 210 to tighten the loop 214 of the ligation element 210 around the anatomical structure 250. In at least one embodiment, an operator may push the pre-tightening sheath 240 towards (i.e., push in the distal direction along the longitudinal axis) the anatomical structure 250 to engage (e.g., contact) the ligation element 210 while keeping the ligation element 210 stationary. In at least another embodiment, an operator may pull the ligation element 210 away (i.e., pull in the proximal direction along the longitudinal axis) from the anatomical structure 250 while keeping the pre-tightening sheath 240 stationary such that the ligation element 210 engages the pre-tightening sheath 240. Further, in at least another embodiment, an operator pulls the ligation element 210 (i.e., pull in the proximal direction along the longitudinal axis) and pushes the pre-tightening sheath 240 (i.e., push in the distal direction along the longitudinal axis) at the same time, or the mechanism, e.g., a trigger, moves both the ligation element 210 and pre-tightening sheath 240 relative to each other (e.g., in opposite directions along the longitudinal axis) at the same time.

The engagement of the distal end 242 of the pre-tightening sheath 240 may cause the effective size of the loop 214 of the ligation element 210 to decrease. As the size of the loop 214 decreases, an operator may potentially reposition the loop 214 to, e.g., achieve a better ligation around the anatomical structure 250.

Figure 2D:
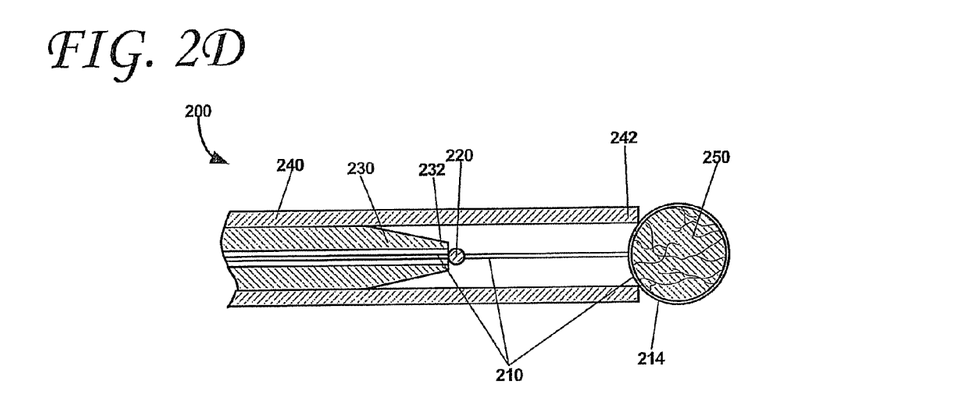
FIG. 2D illustrates a cross-sectional view of the exemplary embodiment of the ligation device of FIG. 2A as the pre-tightening sheath is fully advanced to pre-tighten the ligation element around the structure.

After the loop 214 becomes sufficiently pre-tightened around the anatomical structure 250 as shown in FIG. 2D, an operator may use various techniques to determine whether the loop 214 is located in a desired position. For example, an operator may utilize visualization techniques, e.g., fluoroscopy, ultrasound, magnetic resonance imaging (MRI), computerized tomography (CT), endoscopy, etc. to determine if the loop is properly positioned. Further, for example, an operator may use tactile feed, patient feedback, direct visualization, physiologic response, etc. to determine if the loop is properly positioned. If the operator determines that the loop 214 needs to be relocated, the operator may disengage the pre-tightening sheath from the ligation element 210, thereby loosening the loop 214 around the anatomical structure 250 such that the operator may re-position the loop 214 and re-tighten it. The disengagement may preferably involve movement of the pre-tightening sheath 240 along the longitudinal axis. This process of tightening, loosening, and repositioning may be repeated numerous times.

Figure 2E:
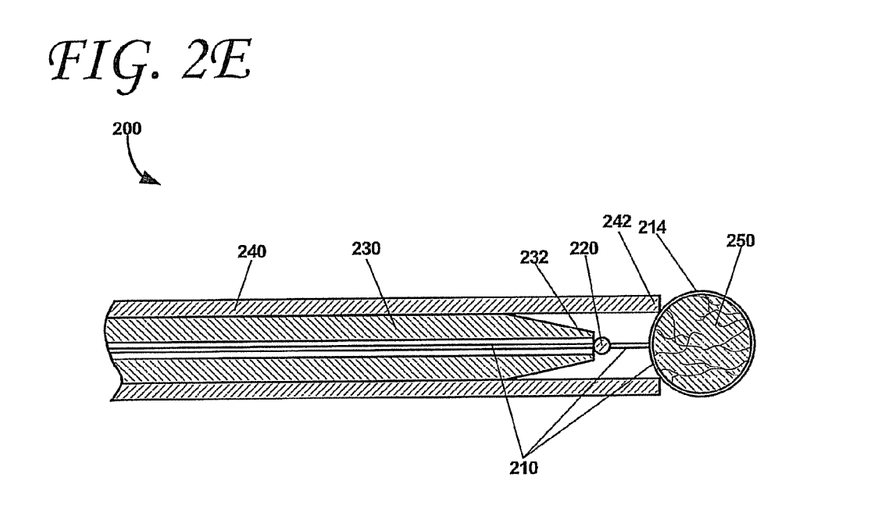
FIG. 2E illustrates a cross-sectional view of the exemplary embodiment of the ligation device of FIG. 2A as the pushing rod is pushing the locking element towards the structure.
Figure 2F:
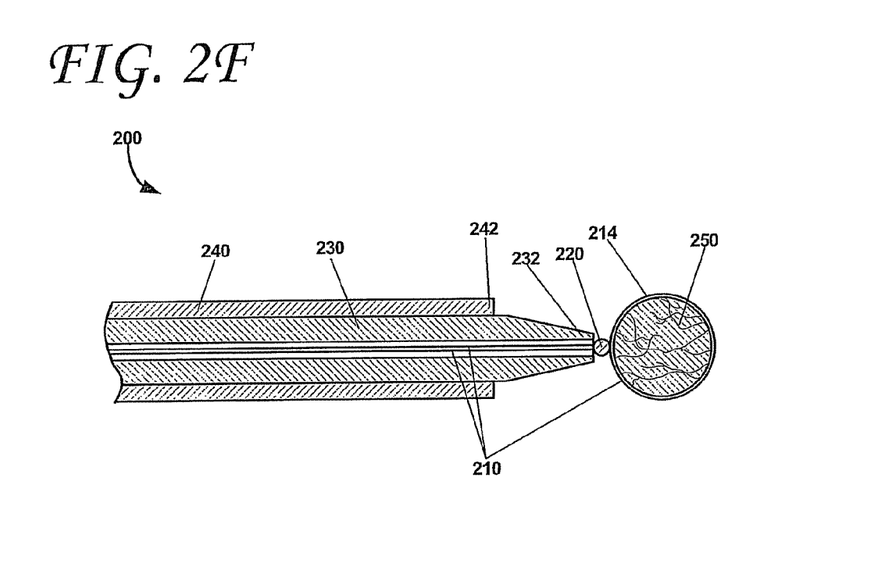
FIG. 2F illustrates a cross-sectional view of the exemplary embodiment of the ligation device of FIG. 2A as the pre-tightening sheath is being retracted after the pushing rod has pushed the locking element to lock the loop of the ligation element around the structure.
Figure 2G:
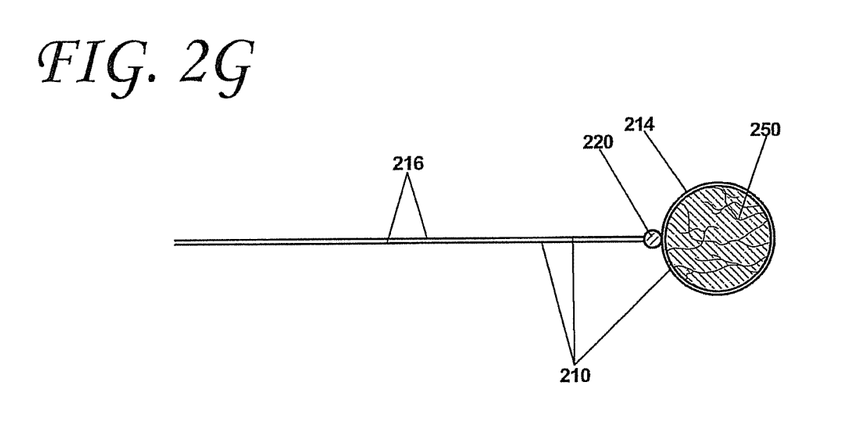
FIG. 2G illustrates a cross-sectional view of the exemplary embodiment of the ligation device of FIG. 2A as the pre-tightening sheath and pushing rod have been fully retracted leaving the ligation element and locking structure with the loop of the ligation element secured around the structure.

After the operator has determined that the loop 214 is properly positioned around the anatomical structure 250, the operator may lock the loop 214. For example, as depicted in FIGS. 2E-G, a locking element 220 may be used to lock the loop 214. In at least one embodiment, the operator may push the locking element 220 with the pushing member 230 towards (i.e., in the distal direction) the anatomical structure 250 while maintaining the ligation element 210 and pre-tightening sheath 240 stationary. In at least another embodiment, the operator may pull the ligation element 210 and pre-tightening sheath 240 away from the anatomical structure (i.e., in the proximal direction) while maintaining the pushing member 230 and locking element 220 stationary. Still, in at least another embodiment, an operator may do both techniques at the same time, e.g., pushing the locking element 220/pushing member 230 (i.e., in the distal direction) and pulling the ligation element 210/pre-tightening sheath 240 (i.e., in the proximal direction), to lock the loop 214 with the locking element 220. Although not shown, ligation device 200 may simplify this process with a mechanism that may move the different parts of the ligation device 100 at, e.g., the push of a button, pull of trigger, etc.

The loop 214 has been locked with the locking element 220 and the pre-tightening sheath 240 has been disengaged from the ligation element 210 in FIG. 2F. The pushing member 230 and pre-tightening sheath 240 have been completely removed in FIG. 2G leaving the loop 214 of the ligation element 210 locked around the anatomical structure with the locking element 220 as well as the remainder 216 of the ligation element 210. The remainder 216 of the ligation element 210 may be removed (e.g., cut using cutting apparatus and then removed) leaving the loop 214 of the ligation element 210 locked around the anatomical structure 250.

Figure 3:
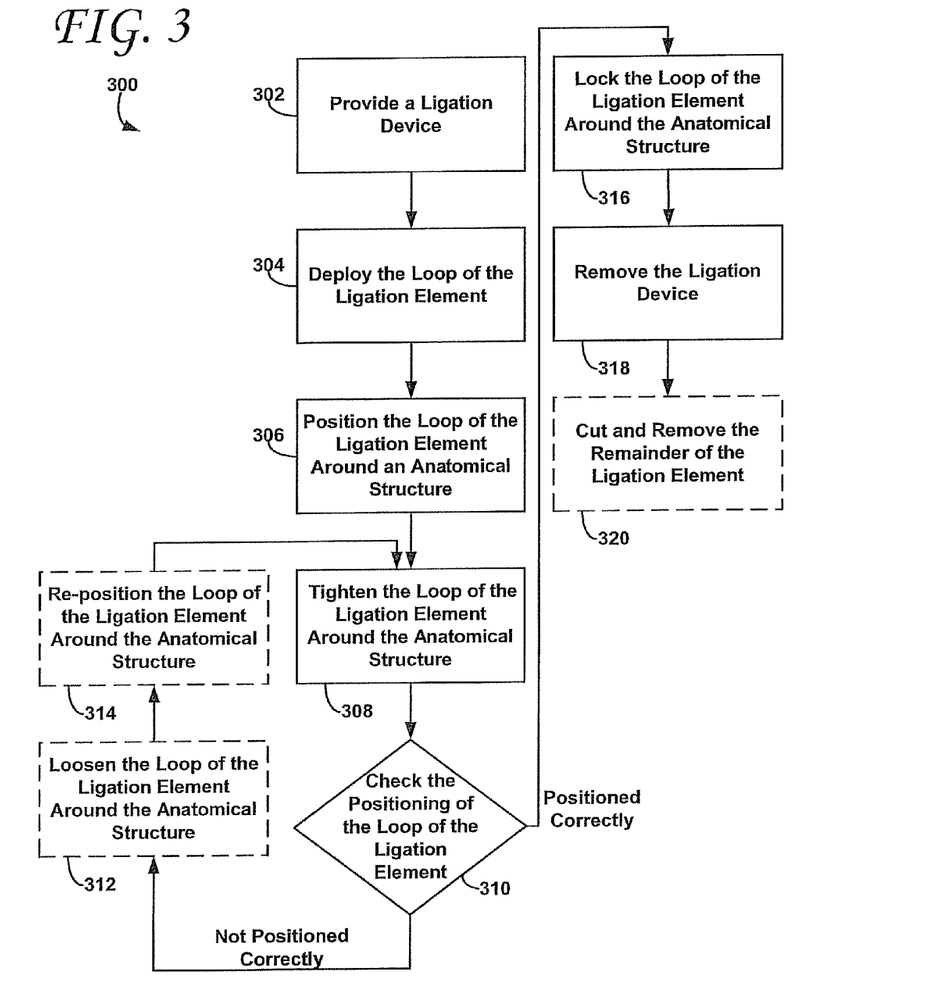
FIG. 3 is a flow chart of an exemplary method of using the ligation device, e.g., the ligation device of FIGS. 2A-G.

FIG. 3 is a flow chart of an exemplary method 300 of using the ligation devices described herein, e.g., the ligation device of FIGS. 2A-G. In this method 300, a ligation device may be provided 302. The ligation device utilized in this method 300 may be the ligation device 200 depicted in FIGS. 2A-G.

The ligation device may be in a pre-deployment position, i.e., the loop may not be exposed such that it may be located around an anatomical structure. As a result, the method 300 may include deploying the loop of the ligation element 304. As previously described herein, either the pre-tightening sheath may be withdrawn in the proximal direction along the longitudinal axis or the ligation element may be advanced distally to deploy the loop of the ligation element.

The method may further include positioning the loop of the ligation element around an anatomical structure 306. An operator may guide the loop around the anatomical structure using only the ligation device, or may use other instruments to assist in positioning the loop. Once the loop appears to be in the proper position, an operator may tighten the loop of the ligation element around the anatomical structure 308 by, e.g., advancing the sheath distally along the longitudinal axis.

The operator may check the position of the loop of the ligation element to verify that the loop is properly positioned and tightened around the anatomical structure 310. If the loop is not properly positioned and/or tightened, the operator may loosen the loop of the ligation element around the anatomical structure 312 (by, e.g., withdrawing the sheath proximally along the longitudinal axis) and re-position the loop around the anatomical structure while the loop is loosened 314. After the loop is re-positioned, the operator may again tighten the loop of the ligation element around the anatomical structure 308 (by, e.g., advancing the sheath distally along the longitudinal axis). Then, again, the operator may check the position/tightness of the loop of the ligation element to verify that the loop is positioned properly around the anatomical structure 310. An operator may tighten, loosen, and re-position the loop of the ligation element until it is properly positioned/tightened.

Once the loop is properly positioned/tightened, the operator may lock the loop of the ligation element to ligate the anatomical structure 316. For example, using the ligation device 200 of FIGS. 2A-G, an operator would lock the loop 214 of the ligation element 210 with the locking element 220. In other embodiments, however, the loop may be locked using adhesive, a suture lock, a knot, RF weld, ultrasonic weld, cryo weld, etc.

After locking the loop of the ligation element around the anatomical structure 316, the ligation device may be removed 318 from, e.g., the patient, and optionally, the remainder of the ligation element, e.g., the portion of the ligation element that does not include the loop, may be cut and removed 320. For example, the remainder of the ligation element may be cut within any suitable cutting device, e.g., a scissors, scalpel, clipper, etc.

Figure 4:
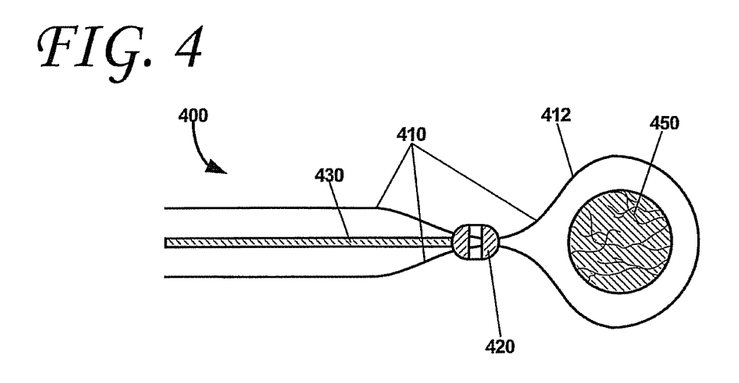
FIG. 4 illustrates a cross-sectional view of another exemplary embodiment of a ligation device.

Another embodiment of ligation device 400 as described herein is depicted in FIG. 4. The ligation device 400 may include a ligation element 410, a locking element 420, and a pushing member 430. The ligation element 410 may include a loop 412 that may be positioned around an anatomical structure 450. Similar to the previously described ligation devices, ligation device 400 may allow an operator to pre-tighten the loop 412 of the ligation element 410 around an anatomical structure 450.

The locking element 420 may be a two-way locking element, e.g., the locking element 420 may be capable of two configurations: a first configuration in which the ligation element 410 may freely move in both the proximal and the distal directions through the locking element 420; and a second configuration in which the ligation element 410 may only move in a single direction (e.g., towards the loop 412 or anatomical structure 450) through the locking element 420. The locking element 420 may be switchable between each configuration by an actuation device, e.g., a button, a switch, trigger, thumb screw, pin etc. located on the locking element 420.

Further, the pushing element 430 may be releasably attached to the locking element 420 by, e.g., a threaded connection, an adhesive connection, a twist-and-lock connection, friction fit, magnetic connection, snap fit, suction fit, etc. Through such coupling, the pushing element 430 may push and/or pull the locking element 420 to tighten and/or loosen the loop. The pushing element 430 may be detached from locking element 420 when, e.g., the locking element 420 has locked the ligation element 410 around the anatomical structure 450. In at least one embodiment, the pushing element 430 may be re-attached to the locking element 420 after detachment.

In at least one embodiment, the two-way locking element 420 may include a ratcheting mechanism. For example, the ligation element may include sloping teeth for the ratcheting mechanism of the two-way locking element to engage, e.g., to tighten and/or loosen, the loop of the ligation element. The ratcheting mechanism may only function in one direction, i.e., the ratcheting mechanism may only tighten the loop of the ligation element (as in, e.g., a wire/cable or "zip" tie). In this case, the ratcheting mechanism may have a release that may be engaged by the operator to allow the operator to loosen the loop of the ligation element.

The complete disclosure of the patents, patent documents, and publications identified herein are incorporated by reference in their entirety as if each were individually incorporated.

Exemplary embodiments of the devices and methods described herein have been discussed and reference has been made to possible variations. These and other variations and modifications will be apparent to those skilled in the art without departing from the scope of the invention, and it should be understood that this invention is not limited to the exemplary embodiments set forth herein. Accordingly, the invention is to be limited only by the claims provided below and equivalents thereof.

What is claimed is:

1. A method of using a ligation device to locate a loop around a structure, wherein the method comprises:
providing a ligation device comprising:
a pre-tightening sheath comprising a proximal end, a distal end, a longitudinal axis extending between the proximal end and the distal end, an opening proximate the distal end of the sheath, and a lumen extending through the sheath from the opening towards the proximal end of the sheath;
a ligation element comprising a loop, wherein at least a portion of the ligation element is located within the lumen of the pre-tightening sheath when the loop extends out of the opening in the pre-tightening sheath, and further wherein the opening in the pre-tightening sheath and the ligation element are sized to allow movement between the pre-tightening sheath and the ligation element to tighten and loosen the loop around the structure located within the loop;
a locking element located within the lumen of the pre-tightening sheath, the locking element operable to retain the loop of the ligation element in a selected size after removal of the ligation element from the pre-tightening sheath; and
a pushing member comprising a proximal end and a distal end, wherein at least a portion of the pushing member is located within the lumen of the pre-tightening sheath, and wherein the pushing member advances the locking element towards the loop of the ligation element when the distal end of the pushing member advances towards the opening of the pre-tightening sheath;
positioning the loop of the ligation element around the structure;
tightening the loop of the ligation element around the structure by moving the pre-tightening sheath and the ligation element relative to each other along the longitudinal axis;
loosening the loop of the ligation element around the structure after the tightening, wherein the loosening comprises moving the pre-tightening sheath and the ligation element relative to each other along the longitudinal axis;
repositioning the loop of the ligation element around the structure; and
locking the loop of the ligation element around the structure with the locking element.

2. The method of claim 1, wherein tightening the loop of the ligation element by moving the pre-tightening sheath and the ligation element relative to each other comprises pushing the pre-tightening sheath along the longitudinal axis towards the loop while holding the loop in a stationary position around the structure.

3. The method of claim 1, wherein tightening the loop of the ligation element by moving the pre-tightening sheath and the ligation element relative to each other comprises pulling the ligation element proximally along the longitudinal axis to move the loop towards the distal end of the pre-tightening sheath.

4. The method of claim 1, wherein locking the loop of the ligation element around the structure with the locking element comprises advancing the locking element distally towards the structure with the pushing member.

5. The method of claim 4, further wherein the ligation element remains stationary while locking the loop of the ligation element around the structure.

6. The method of claim 1, wherein locking the loop of the ligation element around the structure with the locking element comprises pulling the ligation element away from the structure.

7. The method of claim 6, further wherein the locking element and the pushing element remain stationary while locking the loop of the ligation element around the structure.

8. The method of claim 1, wherein the ligation device further comprises cutting apparatus for cutting the ligation element, and wherein the method further comprises cutting the ligation element proximate the locking element with the cutting apparatus.

9. The method of claim 1, wherein the ligation device comprises a restraining mechanism operable between a closed configuration and an open configuration, wherein in the closed configuration the restraining mechanism restricts relative movement between the pre-tightening sheath and the ligation element along the longitudinal axis, and wherein in the open configuration the restraining mechanism allows relative movement between the pre-tightening sheath and the ligation element along the longitudinal axis, wherein the restraining mechanism is located proximate the proximal end of the pre-tightening sheath;

and wherein the method further comprises moving the restraining mechanism from the open configuration to the closed configuration before locking the loop of the ligation element with the locking element.

* * * * *